United States Patent
Balint et al.

(10) Patent No.: US 6,358,699 B1
(45) Date of Patent: Mar. 19, 2002

(54) ASSAY FOR ASYMMETRICAL $N^G$, $N^G$ DIMETHYL-L-ARGININE

(75) Inventors: Robert F. Balint; Mitchell Wayne Mutz; John P. Cooke, all of Palo Alto, CA (US)

(73) Assignees: Cooke Pharma, Silver Springs, MD (US); Panorama Research, Inc., Mountain View, CA (US)

( * ) Notice: Subject to any disclaimer, the term of this patent is extended or adjusted under 35 U.S.C. 154(b) by 0 days.

(21) Appl. No.: 09/495,553

(22) Filed: Feb. 1, 2000

Related U.S. Application Data

(60) Provisional application No. 60/118,838, filed on Feb. 5, 1999.

(51) Int. Cl.[7] .............................. C12Q 1/34; C12Q 1/37; G01N 33/53
(52) U.S. Cl. .............................. 435/18; 435/23; 435/24; 435/962; 435/968; 435/975
(58) Field of Search .............................. 435/18, 23, 24, 435/962, 968, 975

(56) References Cited

FOREIGN PATENT DOCUMENTS

| WO | WO 98/49199 | 11/1998 |
| WO | 2000046395 | * 8/2000 |

OTHER PUBLICATIONS

Bates, et al., *Biochem. J.* (1983), 214(2):593–605.
Bode–Böger, et al., *Biochem. Biophys. Res. Comm.* (1996), 219(2):598–603.
Liu, et al., *Mol. Cell Biol.* (1995), 15(5):2800–8.
MacAllister, et al., *Br. J. Pharmacol.* (1996), 119:1533–40.
Mizobuchi, et al., *Biochem. Biophys. Acta* (1985), 843(1–2):78–82.
Tojo, et al., *Kidney Int* (1997), 52(6): 1593–1601.
Vallance, et al., *J. Cardio. Pharmacol.* (1992), 20(12):S60–2.
Vallance, et al., *Lancet* (1992), 339(8793):572–5.
Yu, et al., *Life Sci.* (1994), 54:753–8.

* cited by examiner

*Primary Examiner*—Louise N. Leary
(74) *Attorney, Agent, or Firm*—Barbara Rae-Venter; Rae-Venter Law Group, P.C.

(57) ABSTRACT

ADMA is determined in a physiological sample by first removing interfering components: proteins by precipitation; and amines and citrulline, by means of a cation exchange column, followed by enzymatic hydrolysis of the ADMA to citrulline with DDAH. The citrulline is then determined spectrophotometrically.

8 Claims, 1 Drawing Sheet

ASSAY FOR ASYMMETRICAL N$^G$, N$^G$ DIMETHYL-L-ARGININE

This is a continuation-in-part application of copending prior application Ser. No. 60/118,838, filed on Feb. 5, 1999.

BACKGROUND

1. EDNO regulates vascular tone.

Endothelium-derived nitric oxide (EDNO) is the most potent endogenous vasodilator known, and, by its effect upon vascular resistance and cardiac contractility, is a major regulator of blood pressure (Moncada and Higgs, 1993; Cooke and Dzau, 1997). NO exerts its effects as a vasodilator, in part, by stimulating soluble guanylate cyclase to produce cGMP. A deficiency of EDNO (as in the endothelial NOS knockout, or with administration of NOS antagonists), causes hypertension (Dananberg et al., 1993; Shesely et al., 1996). An overproduction of nitric oxide (NO) (as in sepsis), causes hypotension and cardiovascular collapse (Rees et al., 1990; Petros et al., 1991).

NO is released from the endothelium in response to a wide variety of physiologic stimuli. For over a century physiologists have recognized that as blood flow increases through a conduit vessel, the vessel dilates. This flow-mediated vasodilation is dependent upon the integrity of the endothelium, and is largely due to the release of EDNO in response to endothelial shear stress (Cooke et al., 1990; Cooke et al., 1991a). Endothelial cells also respond to pharmacological stimuli. Most vasoconstrictors, such as norepinepherine, 5-hydroxytryptamine, and angiotensin II, also stimulate NO release by the endothelium (Moncada and Higgs, 1993; Cooke and Dzau, 1997).

In this way the endothelium modulates vascular contractility. These responses have physiological consequences. For example, during exercise or with mental stress, myocardial oxygen demands increase. In normal individuals the epicardial coronary arteries dilate to accommodate the need for increased coronary blood flow. By contrast, individuals with coronary artery disease have a dysfunctional endothelium with reduced EDNO production and/or activity. In these individuals, a paradoxical coronary artery constriction is observed with exercise or mental stress that contributes to reduced coronary blood flow, resulting in myocardial ischenia (Cox et al., 1989; Zeiher et al., 1989).

In addition to its role as a vasodilator, EDNO is potent inhibitor of vascular smooth muscle (VSM) proliferation. The proliferation of cultured VSM cells is inhibited by exogenous NO donors and cGMP analogues (Garg and Hassid, 1989). Gene transfer of endothelial NOS into the balloon-injured rat carotid artery in vivo demonstrably increases NO release for days after the transfection, and significantly reduces myointimal hyperplasia due to proliferation of intimal vascular smooth muscle cells (von der Leyen, et al., 1995).

EDNO also affects vascular structure by inhibiting the interaction of circulating blood elements with the vessel wall. Platelet adherence and aggregation is inhibited by EDNO (Radomski et al., 1987; Stamler et al., 1989). The adherence and infiltration of leukocytes into the vessel wall during experimental inflammation is reduced by exogenous administration of NO donors, and is enhanced by administration of NOS antagonists (Lefer et al., 1993; Gáboury et al, 1993).

To summarize, in states of vascular injury or inflammation, a deficiency of NO contributes to thrombosis, leukocyte infiltration, and vascular smooth muscle proliferation.

2. The role of NO in atherosclerosis

Atherosclerosis is the major cause of disability in this country and is responsible for 500,000 deaths annually due to coronary artery disease and cerebral vascular attack. Atherosclerosis is accelerated by hyper-cholesterolemia, hypertension, diabetes mellitus, tobacco use, elevated levels of lipoprotein(a) ("Lp(a)") and homocysteine. Intriguingly, all of these disorders are characterized in humans by an endothelial vasodilatory dysfunction well before there is any clinical evidence of atherosclerosis (Cooke and Dzau, 1997). In all of these conditions, the abnormality appears to be due in large part to a perturbation of the NOS pathway. In most of these conditions, the abnormality is reversed or ameliorated by the administration of the NO precursor, L-arginine (Cooke and Dzau, 1997). L-arginine is metabolized by NOS to citrulline and NO.

Dr. John Cooke and coworkers were the first to demonstrate that endothelial vasodilator dysfunction could be reversed by administration of the NO precursor. In hypercholesterolemic rabbits, administration of L-arginine normalizes the NO-dependent vasodilation to acetylcholine (Girerd et al., 1990; Cooke et al., 1991b). Subsequently, Dr. Cooke and others have demonstrated that acute administration of L-arginine can reverse endothelial vasodilator dysfunction that is observed in the coronary and peripheral circulation in patients with atherosclerosis, and in subjects at risk for atherosclerosis.

Because NO has inhibitory effects on many of the key processes that promote atherosclerosis (monocyte adherence, platelet aggregation, vascular smooth muscle proliferation), Cooke postulated that chronic enhancement of vascular NO production could inhibit atherogenesis. Indeed, his lab demonstrated that in hypercholesterolemic rabbits, chronic oral administration of L-arginine could enhance vascular NO activity (Cooke et al., 1992; Wang et al., 1994; Tsao et al., 1994). This effect was associated with a striking reduction in vascular lesions. By contrast, administration of NOS antagonists reduced vascular NO synthesis, increased endothelial adhesiveness for monocytes, and accelerated lesion formation (Tsao et al., 1994; Naruse et al, 1994; Cayatte et al, 1994). Cooke and others have shown that EDNO exerts its effects on atherogenesis by suppressing the expression and the signaling of endothelial adhesion molecules such as VCAM-1, and by reducing the expression of chemokines such as monocyte chemotactic protein-1 (Marui et al., 1993; Tsao et al., in press). The inhibition of adhesion signaling by NO appears to be mediated by cGMP, whereas the transcriptional effects of NO appear to be due, in part, to its abrogation of an oxidant-sensitive transcriptional pathway mediated by NF6B (Marui et al., 1993; Tsao et al., in press; Tsao et al., 1995).

Surprisingly, the administration of L-arginine in hypercholesterolemic rabbits with pre-existing lesions not only slows the progression of disease, but actually induces regression of atherosclerosis (Candipan et al., 1996).

Accordingly, enhancement of vascular NO may represent a novel therapeutic strategy for cardiovascular disease. The initial studies in humans are encouraging. Cooke and others have recently demonstrated that chronic oral administration of L-arginine in hypercholesterolemic humans or those with coronary artery disease can enhance vascular NO activity (as assessed by vascular reactivity studies and measurement of urinary nitrogen oxides), inhibit platelet aggregability, and reduce the adhesiveness of peripheral blood mononuclear cells (Bode-Böger et al., 1994; Wolfe et al., 1995; Theilmeier et al., in press; Lerman et al., 1997).

3. ADMA, a deter minant of endothelial dysfunction and novel risk factor for atherosclerosis ADMA (asymmetric dimethylarginine) is an endogenous antagonist of nitric oxide synthase. Several years ago, Vallance and Moncada demonstrated that, in uremic rats and in patients with renal failure, plasma ADMA levels were elevated 5–10-fold from normal values of about 1 micromolar (Vallance et al., 1992a,b). Plasma from uremic animals and patients (but not controls) induced the constriction of isolated vascular rings. This vasoconstriction was reversed by L-arginine. Moreover, infusions of ADMA into the brachial artery of normal volunteers caused a significant increase in forearm vascular resistance at concentrations of ADMA that are found in patients with renal failure (Vallance et al., 1992b).

Recently, the enzyme that is responsible for degrading ADMA (dimethylarginine dimethylaminohydrolase, or DDAH), has been characterized. An antagonist to DDAH has been developed which blocks ADMA degradation (MacAllister et al., 1996). When the DDAH antagonist is added to vascular rings in vitro, a gradual increase in tone is observed. Again, this vasoconstriction is reversed by L-arginine. These studies suggest that ADMA is continuously being synthesized and degraded. An alteration in the turnover of ADMA can affect NO synthase activity.

Elevated levels of ADMA have been found in patients with hypercholesterolemia and atherosclerosis (Bode-Böger et al., 1996; Yu and Xiong, 1994).

ADMA is formed primarily by methylation of protein arginine inside cells, where it plays an important role in modulating protein-RNA interactions (Liu and Dreyfuss, 1995). Free ADMA is released upon protein turnover, and is probably secreted by most tissues and either passed in the urine or metabolized in the kidney (Tojo et al., 1997). Many types of physiological stress, such as the chronic inflammatory stress associated with atheroma formation, oxidative stress from environmental toxins, and stress which might result from poor nutrition, overweight, or age, is associated with chronic cellular damage and leads to increased rates of protein turnover, which in turn may lead to increased secretion of methylated amino acids and higher circulating levels of these amino acids, including ADMA. Indeed, excretory methylated amino acids have been widely used as markers of protein turnover in, for example, fasting or dystrophic animals (Mizobuchi et al., 1985; Bates et al., 1983).

Virtually all risk factors that are associated with accelerated atherosclerosis are also known to attenuate the synthesis and/or activity of EDNO. As a circulating antagonist of NO biosynthesis, ADMA may be an important determinant of endothelial vasodilator dysfunction, and potentially, an important new risk-factor for atherosclerosis. To further examine the role of ADMA and its importance in cardiovascular disease, methodology must be developed to detect ADMA with greater sensitivity, specificity, and with higher throughput.

Today's standard assay has many shortcomings. The present day method requires high-performance liquid chromatographic separation of all primary amine-containing components of the plasma after they have been derivatized with a fluorescent label, e.g. o-phthalaldehyde. Reproducibility is notoriously sensitive to column and mobile phase conditions and frequent column cleaning and re-running of standard curves is essential. In addition, parallel runs are not easily performed, limiting the number of determinations one can make. Finally, peak areas must be integrated and compared to standard curves.

An immunoassay for ADMA in bodily fluids would normally be desirable for convenience and speed, however, several obstacles hinder the development of accurate antibody-based assays for ADMA in bodily fluids. Chief among these is that any anti-ADMA antibody must be able to distinguish ADMA quantitatively from four structural analogs, which are present in varying amounts in bodily fluids. These include arginine, symmetric $N^G N^G$-dimethyl-L-arginine (SDMA), $N^G$-monomethyl-L-arginine (MMA), and citrulline. Arginine is present in 100-fold excess over ADMA in healthy subjects. SDMA is present in 1–5-fold excess, MMA is present in small amounts, and citrulline is present in 30-fold excess over ADMA. In practice is not realistic to expect high-affinity antibodies to be able to distinguish close analogs by more than a factor of ten or twenty in affinity. However, it is possible to remove most of the arginine and citrulline enzymatically or by solid phase extraction, as described below. SDMA is by far the most troublesome analog as it is an isomer of ADMA with identical molecular weight. SDMA and ADMA cannot be separated by solid phase extraction, are very difficult to separate chromatographically, and would be expected to be very difficult for an antibody to distinguish adequately for accurate measurement of ADMA. Since SDMA has a different physiological provenance from ADMA, and is not an inhibitor of NOS, there is no reason to expect SDMA to correlate with ADMA or to correlate with vascular dysfunction. Therefore, it is absolutely essential to distinguish these analogs, and it would be exceedingly difficult if not impossible to do so with an ADMA immunoassay.

DDAH, however, has at least 1000-fold higher activity toward ADMA than SDMA, and is therefore uniquely suited for use in an enzymatic assay for unequivocal measurement of ADMA in complex mixtures. Nevertheless an enzymatic ADMA assay using DDAH is problematical because of a number of interfering components in blood. Importantly, citrulline is present in blood, so that it would provide a large background which would substantially diminish the accuracy of an assay where citrulline is the final product which is determined as a measure of the amount of ADMA in the sample. In addition, urea which is also present in blood cross-reacts in the citrulline assay. Finally, porphyrins in blood interfere with the spectrophotometric determination of citrulline. In order to have an enzymatic assay using DDAH, it is essential to prevent these various blood components from interfering with the assay.

SUMMARY OF THE INVENTION

An enzymatic assay protocol and compositions are provided for determining ADMA in a blood sample. The method initially removes blood components which may interfere with the assay, e.g. protein removal and enzyme inhibitors or cross-reactive species, followed by concentrating the sample, combining the concentrated sample in the liquid phase with recombinantly prepared $N^G,N^G$-dimethylarginine dimethylaminohydrolase ("DDAH"). Citrulline, the enzymatic product, is then determined colorimetrically. The assay has high reproducibility and accuracy as compared to other assays, which are less convenient and inconvenient to automate.

DESCRIPTION OF THE SPECIFIC EMBODIMENTS

Figure 1:
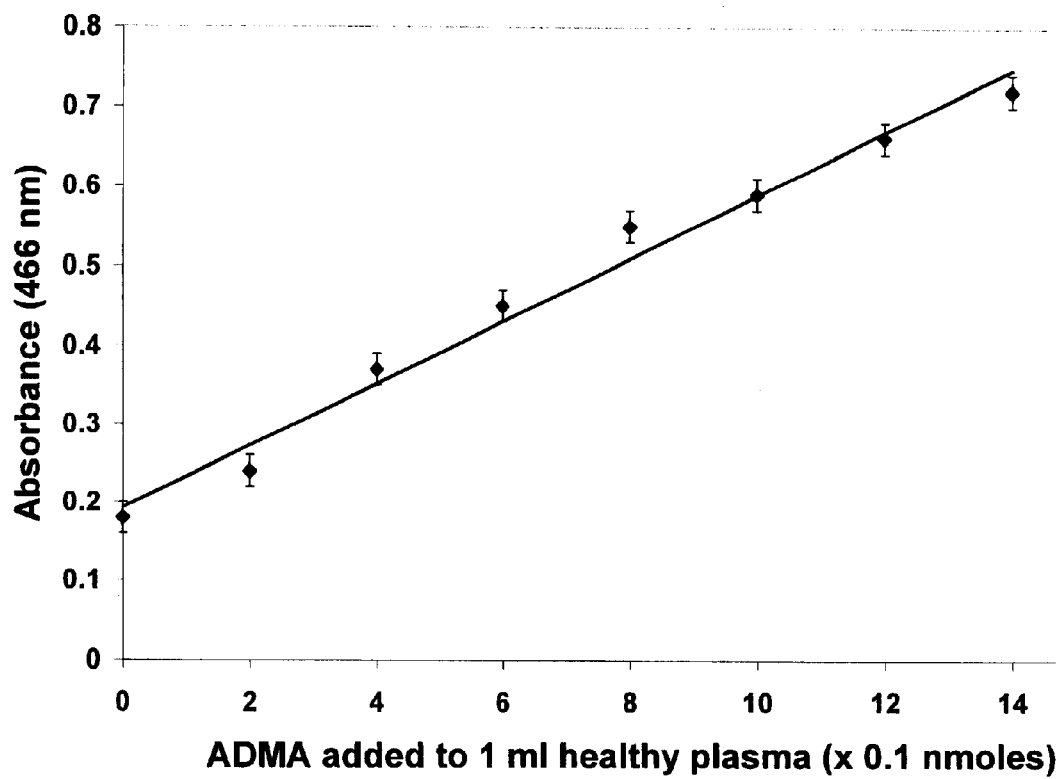
FIG. 1 is a standard curve for determination of ADMA using healthy blood plasma in the indicated amounts and the assays performed in accordance with the protocol in the Experimental on 1 ml aliquots in triplicate.

In accordance with the subject invention, ADMA is accurately assayed in blood samples, prepared as plasma. Plasma is prepared from a blood sample by conventional means. Interfering components of blood are removed in two stages, followed by concentration, enzymatic hydrolysis with recombinant DDAH of the ADMA to citrulline and then spectrophotometrically determining the citrulline in accordance with conventional techniques.

The sample size may be widely varied, generally be in the range of about 0.1 to 5 ml, conveniently 1 ml. Usually, whole blood will not be used, rather plasma or serum.

The first steps of the assay are the removal of interfering components. Citrulline is present in blood and would result in an unacceptable background value. Arginine has approximately 4% of the reactivity of citrulline in the citrulline assay, and as it may be present in 100-fold excess, it is a serious contaminant and must be removed. Normal plasma also contains up to 100 mM urea and other unknown compounds and proteins which cross-react in the citrulline assay, generating background. The background color of porphyrins in plasma interferes with the colorimetric determination of citrulline. In order to have an acceptable assay, it is necessary to negate the effects of these plasma components on the assay.

In the first step the protein present in the plasma is precipitated. This can be achieved using a variety of precipitants (Chambers, J. A. A., in *Biochemistry LABFAX*, J. A. A. Chambers & D. Rickwood, Eds., BIOS Scientific Publishers, Oxford, 1993, pp. 13–17). Generally, organic acids such as acetic, trichloroacetic, perchloric, and sulfosalicylic acids are effective in the range 5–20%, and organic solvents, such as ethanol, methanol, chloroform/isoamyl alcohol (24:1 by vol.), and phenol are also quite effective in the range 1–10 volumes. For example, adjusting the plasma to about 10% trichloroacetic acid ("TCA") is found to be effective, although lower or higher levels of TCA may find use, generally in the range of 5 to 20% TCA. The mixture is centrifuged to provide for a clear demaracation between the precipitant and the supernatant and the supernatant separated.

The standard method for removal of citrulline and urea from plasma is enzymatic hydrolysis (Ceriotti, G. & Gazzaniga, A., 1966, Clinica Chimica Acta 14, 57–62). Citrulline is hydrolyzed to ornithine and carbamyl arsenate by ornithine carbamyltransferase in the presence of arsenate, and urea is converted to $CO_2$ and ammonia by urease. Arginine may also be removed rapidly and quantitatively by treatment with 1000 units of arginase (Sigma A8013) for 5–10 minutes at room temperature. For a high-throughput assay of ADMA enzymatic removal of citrulline and urea cumbersome. As a result, a novel solid phase extraction procedure (SPE) is employed, by which ADMA could be quantitatively recovered from plasma in a single step with quantitative removal of citrulline, urea, and other compounds which interfere with citrulline determination. Solid phase extraction of ADMA from plasma may be accomplished using either cation exchange or reversed phase. However, by combining the two methods with e.g., a mixed phase medium containing silica-bonded hydrocarbon and acyl groups, a quantitative separation of ADMA from citrulline, urea, and other compounds which interfere with citrulline determination may be achieved in a single step.

To allow SPE of ADMA directly from acidic solutions, such as 10% TCA, a strong cation exchanger such as sulfonate is necessary. Thus, a convenient medium for this purpose is benzenesulfonic acid bonded to silica (SCX), and the use of SCX will be described as exemplary. SCX cartridges from e.g., Varian, are compatible with a variety of formats, including 96-well and standard vacuum manifolds for solid phase extraction. Upon loading, most cations and many hydrophobic compounds will be retained on SCX. However, cations of weak to moderate strength having moderate polarities, such as citrulline, are efficiently removed by washing with alkaline buffer, while ADMA is quantitatively retained by virtue of both charge and hydrophobic interaction. This degree of separation of analogues is quite unusual for SPE, and was not expected because $N^G$-monomethylarginine, which differs from ADMA by a single methyl group and has a higher guanidino $pK_a$, is nevertheless not retained on the same sorbent during the pH8 wash, presumably due to its slightly higher polarity.

After the pH8 wash, the column is washed with solvent to remove neutral hydrophobics, leaving only strong cations with low polarity, such as ADMA, bound. Finally, the ADMA may be quantitatively eluted with an alkaline solvent such as alcohol triethylamine or ammonium hydroxide, leaving behind all residual polar compounds. The column volume will generally be in the range of 0.1 to 2.0 times the volume of the original sample. One conditions the column with methanol, followed by water and then dilute acid. The volumes will generally be in the range of 10 to 30 times the column volume. The sample may then be applied under differential pressure, positive or negative to drive the sample through the column. The ADMA is retained on the column. The column may then be washed with a mildly acidic solution, followed by mildly basic buffer (pH7.5–9) and methanol. Specifically, a 2% trichloroacetic acid solution is followed with potassium phosphate pH8 and then methanol. The ADMA may be eluted from the column using methanolic hydroxide. Conveniently, dilute triethylamine (1–5% aqueous) is mixed with methanol to form a mixture of from about 50–80% methanol.

In the next step, the eluate is concentrated using evaporation under nitrogen and may be concentrated to dryness in vacuo under mild conditions, e.g. ambient temperatures in a nitrogen-purged Speed-Vac evaporator (Savant), conditions which avoid loss of any ADMA. Purging the system with nitrogen before and during evaporation avoids oxidation of the guanidino nitrogens of ADMA. The samples are then dissolved in assay buffer, which is convenient for the enzymatic hydrolysis by DDAH. A mildly acidic buffer is used which neutralizes the residual base, conveniently a phosphate buffer, pH 5.5–6.5. 0.01 unit of DDAH is more than sufficient for complete hydrolysis of 0.5 nmole of ADMA at 30 min at 42° C., and may be proportionately modified in accordance with the volume of the sample and the anticipated range of ADMA. Depending on the prior treatment of the sample, e.g. dilution and assay medium volume, and the volume of the plasma sample, the amount of enzyme may be adjusted accordingly to provide a reasonable time period for the assay. Generally, the time period for the hydrolysis reaction will be in the range of about 30 to 120 min, more usually about 60 min. Shorter times will be associated with smaller volumes and lower concentrations of ADMA.

Many chromogenic reactions of citrulline have been described, most of which depend on condensation of an aldehyde or ketone with the urea group of citrulline in acidic solution, followed by oxidation to form a colored cyclic product (Fearon 1939, Biochem. 33, 902–7). A widely used variant of this assay is based on a highly specific condensation of urea groups with diacetyl monokime and antipyrine to produce an orange product with an absorbance maximum at 466 nm (Prescott and Jones 1969, Anal. Biochem. 32, 408–19). Color development is initiated by adding directly to the DDAH reaction mixture a chromogenic reagent that reacts specifically with urea groups. A common reagent consists of 0.5% anti-pyrine in 50% sulfuric acid and 0.8% diacetyl monoxime in 5% acetic acid (Prescott and Jones 1969 Anal. Biochem. 32, 408–19). Color development takes about 90 min at 75–90EC, after which time the samples are cooled to room temperature where the color is stable. Absorbance may be determined in a spectrophotometer at 466 nm, where 1 nmole of citrulline gives an $A_{466}$ of ~0.6.

To obtain a value for the amount of ADMA, assays with control samples of known amounts of ADMA are performed to obtain a standard curve, with the amount of ADMA graphed against observed signal. This curve can then be used to read the amount of ADMA present in the sample from the signal observed from the assay.

Other assays may be used to determine the final citrulline concentration. For example, the material is so clean at this stage that citrulline can be quantified in less than 15 min. by reversed phase HPLC using a 5 cm $C_{18}$ column with acetonitrile in potassium phosphate pH 6.5 as the mobile phase. Detection is accomplished by pre-column in-line derivatization of primary amino groups with 0-phthalaldehyde and post-column in-line fluorometry, illuminating in the far uv and detecting emission at 450 nm. Citrulline is quantified by peak integration and comparison with a standard curve. Recovery is determined by an internal standard such as homoarginine. Another commonly used assay for citrulline involves enzymatic conversion to ornithine, $NH_3$ and $CO_2$ using ornithine carbamyl transferase in the presence of AMP or ADP to inhibit the forward reaction. Product ammonia is stoichiometric for citrulline and is determined by the standard clinical method. Glutamate dehydrogenase is used to aminate α-ketoglutarate to glutamate plus $H_2O$ with oxidation of NADPH, which is measured spectrophotometrically.

Kits can be provided which comprise the reagents necessary for carrying out the assay, including DDAH, and optionally buffers, acid solutions, chromogenic reagents and the like. In addition, kits may include devices for processing many samples in parallel. For example, solid phase extraction manifolds are commercially available in 8×12 array (96-well) microtiter formats (e.g., Empore™, 3M Corp.; SPE Microlute™, Varian Corp.). Typically, these devices include extraction disk plates in which up to 2 ml fluid may be loaded into each well. At the bottom of each well is a pre-filter array to trap particulates, including precipitated protein. Beneath the pre-filter, is an extraction disk comprised typically of bonded silica sorbents embedded in a membrane. Beneath each extraction disk is an opening to allow flow-through. Flow-through may be driven by centrifugation, positive pressure, or by vacuum after attaching the plate to a vacuum manifold. After conditioning of the sorbent, plasma samples (up to 2 ml) may be added to the wells, and protein precipitated by acidification before initiating flow-through. During flow-through, precipitated protein is retained on the pre-filter as the remaining solutes enter the extraction disk. With larger samples precipitated protein may inhibit flow. In this case, one may use two extraction plates. The first 96-well plate may contain the pre-filter only, to retain the precipitate, and the flow-through may be collected directly in a second extraction plate containing the pre-conditioned cation exchange or mixed phase sorbent. After washing, ADMA may be eluted from the extraction disks directly into a 96-well collection plate or a rack of 96 microcentrifuge tubes. Collection plates or tube racks may then be fitted directly into 96-well plate holders in a vacuum centrifuge (e.g., Jouan Corp.) for evaporation. After evaporation, sample residues are dissolved directly in DDAH buffer and, after addition of DDAH, ADMA hydrolysis may be carried out directly in the collection plate. After the DDAH reaction, color development may also be carried out directly in the collection plate by addition of the chromogenic reagents. Finally, a spectrophotometric microtiterplate reader (e.g., Bio-Rad Corp.) can be used to obtain absorbance measurements directly in the collection plates.

Additional gains in throughput may be made by automation of the procedure, which also reduces human error in pipetting and other procedural steps. Many commercially available liquid handling workstations are specifically designed to accommodate the 96-well microtiter format (e.g., Packard, Beckmann, Hamilton, Tomtec). These workstations can eliminate all of the manual steps in this assay with the possible exception of the evaporation step. The latter would only require manual removal of the collection plates from the robot, placement in the vacuum centrifuge, and after drying, replacement back into the robot for the enzyme reaction, color development, and absorbance measurement steps. One may also automate the evaporation step since elution volumes from extraction disks are typically quite small and some workstations are equipped with heating devices that can drive off small volumes of solvent quite efficiently. The aqueous residue may then be diluted directly in DDAH buffer for the enzyme reaction and subsequent steps without removing the collection plate from the robot.

DDAH ($N^G,N^G$-dimethylarginine dimethylaminohydrolase; EC3.5.3.18) was first described in rat kidney (Ogawa et al., 1989) and was subsequently cloned and sequenced (Kimoto et al., 1997). Expression of recombinant DDAH in E. coli generally results in low yields of soluble active enzyme, the bulk of the gene product aggregating into insoluble inclusions (Mutz and Balint, unpublished). Attempts to refold DDAH from solubilized inclusions are difficult (Mutz and Balint, unpublished). However, improved yields could be achieved by expression of DDAH as a fusion with stable bacterial proteins such as Glutathione S-transferase (GST) (Mutz and Balint, unpublished; Kaelin et al., 1992; Smith & Johnson, 1988). For example, expression of the DDAH-GST fusion from a pBR322-derived vector in E. coli yields approximately 10 mg (12 units) of the active enzyme per gram of cells after purification by affinity chromatography on immobilized glutathione.

The following examples are offered by way of illustration and not by way of limitation.

EXPERIMENTAL

The exemplary assay procedure is as follows:
1. From each 1 ml aliquot of plasma, arginine is removed by adding 1000 units arginase (Sigma) and incubating at room temperature for 5–10 min., after which protein is precipitated by adjusting to 10% trichloroacetic acid (TCA), and removed by micro-centrifugation at 12,000×g for 15 minutes.
2. The supernatant from step (1) is then applied directly to any of a number of commercially available mixed phase cation exchange and hydrophobic interaction matrices. A convenient one is the SCX cartridge made by Varian, which is available in 96-well format, and which is compatible with standard vacuum and positive pressure manifolds for solid phase extraction. For this application the cartridge may be conditioned with 1 ml methanol (MeOH), followed by 3 ml H$_2$O and then 2 ml 2% TCA. Sample is then applied under moderate pressure or vacuum. ADMA is retained, and after washing with 2 ml 2% TCA, 3 ml 50 mM potassium phosphate, pH8, and 1 ml MeOH, ADMA is quantitatively eluted in 1.7 ml per sample of 2% triethylamine in 70% methanol.

3. Concentration of the samples at this stage facilitates the enzymatic step, and is essential for accurate calorimetric determination of the final product, citrulline. Concentration is rapidly accomplished by centrifugal flash evaporation in a Speed-Vac evaporator (Savant) after purging with nitrogen.

4. The samples are then re-dissolved in potassium phosphate buffer, pH6.5, to a final concentration of 50 mM in a final volume of 100 µl after addition of purified recombinant DDAH. 0.01 unit per sample (1/1200 of a 1-liter prep) is more than sufficient for complete hydrolysis of 0.5 nmole ADMA in 30' at 420° C.

5. Color development is initiated by adding directly to the DDAH reaction 50 µl of a chromogenic reagent that reacts specifically with urea groups, consisting of an equal mixture of 0.5% anti-pyrine and 10 mM FeSO$_4$ in 50% sulfuric acid and 0.8% diacetyl monoxime in 5% acetic acid (Prescott & Jones, 1969 *Anal. Biochem.* 32, 408–19). Color development takes 40' at 85° C. after which the samples are cooled to room temperature where the color is stable. The absorbance is determined in a spectrophotometer at 466 nm, where 1 nmole of citrulline gives an A$_{466}$ of ~0.6.

The following is a summary of the steps for the assay.

Enzymatic Assay for ADMA in Plasma

1. Acid precipitate protein & centrifuge
2. Mixed phase cation exchange and hydrophobic interaction cartridge to remove background
3. Centrifugal flash evaporation to concentrate
4. DDAH treatment to convert ADMA to citrulline
5. Colorimetric determination of citrulline To construct a standard curve, authentic ADMA (Sigma) was added to human blood plasma from a healthy patient in amounts of 0.2, 0.4, 0.6, 0.8, 1.0, 1.2, and 1.4 nmoles per ml. The assay was performed in triplicate and the results are shown in FIG. 1. The slope (0.039 A$_{466}$ per nmole) and the y-intercept (0.19 A$_{466}$) of the fitted curve indicate that the plasma contained 0.47 nmoles per ml ADMA. This was in agreement with values reported in the literature and confirmed using the standard method, which involved fluorescent labeling with O-phthalaldehyde, reversed phase high performance liquid chromatography (HPLC), and post-column, in-line fluorometric detection (Böger et al., 1998 *Circulation* 98, 1842–1847; Chen et al., 1997 *J Chromatogr B Biomed Appl* 692, 467–471). Table 1 shows a comparison of the standard assay and the enzymatic assay for a series of plasma samples from six at-risk patients. The two methods are in excellent agreement. In addition, standard errors are considerably lower with the enzymatic assay.

TABLE 1

Comparison of the Standard Method and the Enzymatic Method for Determination of ADMA in Plasma from six at-risk patients.

| Patient # | Standard Method | Enzymatic Method |
|---|---|---|
| 1 | 0.76 ± 0.15 µM | 0.65 ± 0.04 µM |
| 2 | 1.96 ± 0.36 µM | 2.11 ± 0.12 µM |
| 3 | 1.68 ± 0.30 µM | 1.48 ± 0.08 µM |
| 4 | 0.76 ± 0.14 µM | 0.84 ± 0.05 µM |
| 5 | 0.91 ± 0.17 µM | 0.82 ± 0.04 µM |
| 6 | 0.62 ± 0.13 µM | 0.67 ± 0.04 µM |

It is evident from the above description and results that the subject protocol is greatly superior to the presently available procedures for measuring ADMA. The subject protocol avoids immunoassays which would have the difficulty of identifying ADMA in the presence of greater amounts of L-arginine and symmetrical L-N$^G$,N$^G$-dimethyl arginine. The subject method avoids the use of a sophisticated high-performance liquid chromatographic (HPLC) separation of all primary amine-containing components of the plasma after they have been derivatized with a fluorescent label, where reproducibility is notoriously sensitive to column and mobile phase conditions and frequent column cleaning and re-running of standard curves is essential. In addition, peak areas must be integrated and compared to standard curves. In addition, the use of the HPLC does not permit parallel samples to be run, substantially reducing the number of assays that can be performed with a single piece of equipment.

All publications and patent applications mentioned in this specification are herein incorporated by reference to the same extent as if each individual publication or patent application was specifically and individually indicated to be incorporated by reference.

The invention now fully described, it will be apparent to one of ordinary skill in the art that many changes and modifications can be made thereto without departing from the spirit or scope of the appended claims.

LITERATURE CITED

Balint R F and Larrick J W (1993) Antibody engineering by parsimonious mutagenesis. Gene 137: 109–118

Balint R F and Plooy I. (1995) Protease-dependent streptomycin sensitivity in *E coli:* a method for identifying protease inhibitors. Bio/Technology 13: 507–510

Bates P C, Grimble G K, Sparrow M P, Millward D J. Myofibrillar protein turnover. Synthesis of protein-bound 3-methylhistidine, actin, myosin heavy chain and aldolase in rat skeletal muscle in the fed and starved states. Biochem J 1983 August 15;214(2):593–605

Bode-Böger S M, Böger R H, Creutzig A, Tsikas D, Gutzki F M, Alexander K, Frolich J C. L-arginine infusion decreases peripheral arterial resistance and inhibits platelet aggregation in healthy subjects. Clin Sci 1994;87(3): 303–10

Bode-Böger S M, B6ger R H, Thiele W, Junker W, Frolich J C. Elevated L-arginine/dimethylarginine ratio contributes to enhanced systemic NO production by dietary L-arginine in hypercholesterolemic rabbits. Biochem Biophys Res Comm 1996;219(2):598–603

Böger R H, Bode-Böger S M, Thiele W, Junder W, Alexander K, Frölich J C: Biochemical evidence for impaired nitric oxide synthesis in patients with peripheral arterial occlusive disease. Circulation 1997a; in press Böger R H, Bode-Böger S M, Szuba A, Tsao P S, Chan J R, Tangphao O, Blaschke T F, Cooke J P: ADMA: A novel risk factor for endothelial dysfunction, its role in hypercholesterolemia. N Engl J Rev 1997b; submitted for review Burke T, Bolger R, Checovich W, and Lowery R. In: Phage Display of Peptides and Proteins, A Laboratory Manual, Kay B, Winter J, McCafferty J, Eds., Academic Press, San Diego, 1996, pp.305–326.

Candipan R C, Wang B-Y, Tsao P S, Cooke J P. Regression or progression: dependency upon vascular nitric oxide activity. Arter, Throm, Vas Bio 1996;16:44–50

Cayatte A J, Palacino J J, Horten K, Cohen R A. Chronic inhibition of nitric oxide production accelerates neointima formation and impairs endothelial function in hypercholesterolemic rabbits. Arterioscler Thromb 1994; 14:753–759

Chen B M, Xia L W, Zhao R Q. Determination of N(G),N (G)-dimethylarginine in human plasma by high-performance liquid chromatography. J Chromatogr B Biomed Sci Appl 1997 May 9;692(2):467–471

Cooke J P, Rossitch E, Andon N, Loscalzo J, Dzau V J: Flow activates an endothelial potassium channel to release an endogenous nitrovasodilator. J Clin Invest 1991a;88:1663–1671

Cooke J P, Stamler J S, Andon N, Davies P F, Loscalzo J: Flow stimulates endothelial cells to release a nitrovasodiator that is potentiated by reduced thiol. Am J Physiol [Heart Circ Physiol] 1990; 28:H804–H812, 1990

Cooke J P, Andon N A, Girerd X J, Hirsch A T, Creager M A: Arginine restores cholinergic relaxation of hypercholesterolemic rabbit thoracic aorta. Circulation 1991b;83:1057–62

Cooke J P, Singer A H, Tsao P, Zera P, Rowan R A, Billingham M E: Anti-atherogenic effects of L-arginine in the hypercholesterolemic rabbit. J Clin Invest 1992;90:1168–1172

Cooke J P, Dzau V J: Nitric oxide synthase: Role in the genesis of vascular disease. Annu Rev Med 1997;48:489–509

Coty W A, Loor R, Powell M J, Khanna P L (1994) CEDIA homogeneous immunoassays: current status and future prospects. J Clin Immunoassay 17: 144–150.

Cox D A, Vita J A, Treasure C B, Fish R D, Alexander R W, Ganz P, Selwyn A P: Atherosclerosis impairs flow-mediated dilation of coronary arteries in humans. Circulation 1989;80:458–465

Creager M A, Girerd X J, Gallagher S J, Coleman S, Dzau V J, Cooke J P: L -arginine improves endothelium-dependent vasodilation in hypercholesterolemic humans. J Clin Invest 1992;90:1248–1253

Dananberg J, Sider R S, Grekin R J: Sustained hypertension induced by orally administered nitro-L-arginine. Hypertension 1993;21:359–363 den Hartog M, Balint R, Larrick J, deBoer M. Generation of a humanized anti-CD40 MAb for treatment of autoimmune diseases. Keystone Antibody Engineering Meeting, Taos, N.Mex. (1996)

Drexler H, Zeiher A M, Meinzer K, Just H. Correction of endothelial dysfunction in coronary microcirculation of hypercholesterolemic patients by L-arginine. Lancet 1991; 338: 1546–1550.

Fägerstam L G, Frostell-Karlsson Å, Karlsson R, Persson B, Rönnberg I. (1992) J Chromatog 597: 397–410.

Gaboury J, Woodman R C, Granger D N, Reinhardt P, Kubes P. Nitric oxide prevents leukocyte adherence: role of superoxide. Am J of Physio 1993;265(3 Pt 2):H862–7

Garg U C, Hassid A. Nitric oxide-generating vasodilators and 8-bromo-cyclic guanosine monophosphate inhibit mitogenesis and proliferation of cultured rat vascular smooth muscle cells. J Clin Invest 1989;83:1774–1777

Girerd X J, Hirsch A T, Cooke J P, Dzau V J, Creager M A. L-arginine augments endothelium-dependent vasodilation in cholesterol-fed rabbits. Circ Res 1990;67:1301–1308

Harlow E and Lane D Antibodies A Laboratory Manual Cold Spring Harbor Laboratory, Cold Spring Harbor, N.Y., 1988.

Henderson D R, Friedman S B, Harris J D, Manning W B, Zoccoli M A CEDIA, a new homogeneous immunoassay system. (1986) Clin Chem 32: 1637–1641.

Hoogenboom H R, Griffiths A D, Johnson K S, Chiswell D J, Hudson P, Winter G (1991) Nucl. Acids Res. 19:4133–4137

Hoogenboom H R Designing and optimizing library selection strategies for generating high-affinity antibodies. Trends Biotechnol 1997 February;15(2):62–70

Jacobson R H, Zhang X J, Dubose R F, Matthews B W (1994) Three-dimensional structure of beta-galactosidase from *E coli.* Nature 369: 761.

Janknecht R, de Martynoff G, Lou J, Hipskind R A, Nordheim A, Stunnenberg H F. (1991) Rapid and efficient purification of native histidine-tagged protein expressed by recombinant vaccinia virus. Proc. Natl. Acad. Sci. (USA) 88:8972–8976

Kalnins A, Otto K, Ruther U, Muller-Hill B. (1983) Sequence of the lacZ gene of *Escherichia coli.* EMBO J 2: 593–597

Kay B, Winter J, McCafferty J Phage Display of Peptides and Proteins, A Laboratory Manual Academic Press, San Diego, 1996.

Kopetski E, Lehnert K, Buckel P (1994) Enzymes in diagnostics: achievements and possibilities of recombinant DNA technology. Clin. Chem. 40: 688–704

Larrick J W, Truitt K E, Raubitschek A A, Senyk G, Wang J C N (1983) Characterization of human hybridomas secreting antibody to tetanus toxoid. Proc. Natl. Acad. Sci. (USA) 80: 6376.

Larrick J W, Graham D, Chenoweth D E, Kunkel S, Fendly B M, Deinhart T. (1986) Murine monoclonals recognizing neutralizing epitopes on human C5a. Infet. Immun. 55:1867.

Larrick J W, Wallace E F, Coloma M J, Bruderer U, Lang A B, Fry K E. (1993) Therapeutic human antibodies derived from PCR amplification of B cell variable regions. Immunological Reviews 130: 69–85.

Larrick J W and Balint, R F. Recombinant therapeutic human monoclonal antibodies. In: The Pharmacology of Monoclonal Antibodies. Handbook of Experimental Pharmacology. M. Rosenberg and G. Moore (eds). Academic Press, New York, 1993.

Lauritzen E, Flyge H, and Holm A. In: Antibody Techniques. V S Malik and E Lillehoj, Eds., Academic Press, San Diego, 1994, pp. 227–258.

Lefer A M, Siegfried M R, Ma X L. Protection of ischemia-reperfusion injury by sydnonimine NO donors via inhibition of neutrophil-endothelium interaction. J of Card Pharm 1993;22 Suppl 7:S27–33

Lerman A, McKinley L, Higano S T, Holmes D R: Oral chronic L-arginine administration improves coronary endothelial function in humans. JACC 1997;29(2)

Liu Q, Dreyfuss G. In vivo and in vitro arginine methylation of RNA-binding proteins. Mol Cell Biol 1995 May;15(5): 2800–2808

MacAllister R J, Parry H, Kimoto M, Ogawa T, Rusell R J, Hodson H, Whitley G S J, Vallance P: Regulation of nitric oxide synthesis by dimethylarginine dimethylaminohydrolase. Br. J. Pharmacol. 1996;119:1533–1540

Marks J D, Tristem M, Karpas A, and Winter G. 1991a. Oligonucleotide primers for polymerase chain reaction amplification of human immunoglobulin variable genes and design of family-specific oligonucleotide probes. Eur. J. Immunol. 21,985–991.

Marks J D, Hoogenboom H R, Bonnert T P, McCafferty J, Griffiths A D, and Winter G. 1991b. By-passing immunization: Human antibodies from V-gene libraries displayed on phage. J. Mol. Biol. 222, 581–597.

Marui N, Offerman M K, Swerlick R, Kunsch C, Rosen C A, Ahmad M, Alexander R W, Medford R M. Vascular cell adhesion molecule-1 (VCAM-1) gene transcription and expression are regulated through an antioxidant-sensitive mechanism in human vascular endothelial cells. J Clin Invest 1993;92:1866–1874

McCafferty J. Phage Display: Factors Affecting Panning Efficiency. In: Phage Display of Peptides and Proteins, Kay B, Winter J, McCafferty J, eds. Academic Press, San Diego, 1996, pp.261–276.

McCafferty J and Johnson K. Construction and screening of antibody display libraries. In: Phage Display of Peptides and Proteins, Kay B, Winter J, McCafferty J, eds. Academic Press, San Diego, 1996, pp.79–112.

Mizobuchi M, Inoue R, Miyaka M, Kakimoto Y. Accelerated protein turnover in the skeletal muscle of dystrophic mice. Biochim Biophys Acta 1985 November 22;843(1–2):78–82

Moffatt B A and Studier F W (1986) J Mol Biol 189: 113–130

Moncada S, Higgs E A: The L-arginine-nitric oxide pathway. N Engl J Med 1993;329:2002–2012

Naruse K, Shimizu K, Muramatsu M, Toki Y, Miyazaki Y, Okumura K, Hashimoto H, Ito T. Prostaglandin H2 does not contribute to impaired endothelium-dependent relaxation and long-term inhibition of nitric oxide synthesis promotes atherosclerosis in hypercholesterolemic rabbit thoracic aorta. Arterioscler Thromb 1994; 14:746–752

Petros A, Bennett D, Valiance P: Effect of nitric oxide synthase inhibitors on hypotension in patients with septic shock. Lancet 1991;338:1557

Radomski M W, Palmer R M J, Moncada S. Comparative pharmacology of endothelium-derived relaxing factor, nitric oxide, and prostacyclin in platelets. Br J Pharmacol 1987;92:181–187

Rees D D, Cellek S, Palmer R M J, Moncada S: Dexamethasone prevents the induction by endotoxin of a nitric oxide synthase and the associated effects on vascular tone: an insight into endotoxin shock. Biochem and Biophys Res Com 1990;173:541–547

Sambrook J, Frisch E F, Maniatis T, Molecular Cloning A Laboratory Manual 2nd Ed. Cold Spring Harbor Laboratory, Cold Spring Harbor, N.Y., 1989.

Schier R, Balint R F, McCall A, Apell G, Larrick J W, Marks J D. (1996) Identification of functional and structural amino-acid residues by parsimonious mutagenesis Gene 169: 147–155

Scott J K and Smith G P (1990) Searching for peptide ligands with an epitope library. Science 249: 386–390

Shesely E G, Maeda N, Kinm H S, Desai K M, Krege J H, Laubach V E, Sherman P A, Sessa W C, Smithies O: Elevated blood pressures in mice lacking endothelial nitric oxide synthase. Proc Nat Acad Sci USA 1996;93(23):13176–81

Short J et al. (1988) Nucleic Acids Res. 16: 7583–7600.

Sparks A B, Adey N B, Cwirla S, Kay B K Screening phage-displayed random peptide libraries. In: Phage Display of Peptides and Proteins, Kay B, Winter J, McCafferty J, eds. Academic Press, San Diego, 1996, pp. 227–254.

Stamler J S, Mendelsohn M E, Amarante P, Smick D, Andon N, Davies P F, Cooke J P, Loscalzo J: N-acetylcysteine potentiates platelet inhibition by endothelium-derived relaxing factor. Circ Res 1989;65:789–795

Theilmeier G, Zalpour C, Ma A, Anderson B, Wang B-Y, Wolf A, Candipan R C, Tsao P S, Cooke J P. Adhesiveness of mononuclear cells in hypercholesterolemic humans is normalized by dietary arginine. Arter, Throm, Vas Bio (submitted)

Tojo A, Welch W J, Bremer V, Kimoto M, Kimura K, Omata M, Ogawa T, Vallance P, Wilcox C S. Colocalization of demethylating enzymes and NOS and functional effects of methylarginines in rat kidney. Kidney Int 1997 December;52(6):1593–1601

Tsao P, McEvoy L M, Drexler H, Butcher E C, Cooke J P: Enhanced endothelial adhesiveness in hypercholesterolemia is attenuated by L-arginine. Circulation 1994;89:2176–2182

Tsao P S, Lewis N, Alpert S, Cooke J P. Exposure to shear stress alters endothelial adhesiveness: Role of nitric oxide. Circulation 1995;92:3513–3519

Tsao P, Buitrage R, Chan J S, Cooke J P. Fluid flow inhibits endothelial adhesiveness: NO and transcriptional regulation of VCAM-1. Circulation (in press)

Vallance P, Leone A, Calver A, Collier J, Moncada S: Endogenous dimethyl-arginine as an inhibitor of nitric oxide synthesis. J Cardiovasc Pharmacol 1992a;20(Suppl. 12):S60–S62

Vallance P, Leone A, Calver A, Collier J, Moncada S. Accumulation of an endogenous inhibitor of nitric oxide synthesis in chronic renal failure. Lancet 1992b;339(8793):572–5 von der Leyen H E, Gibbons G H, Morishita R, Lewis N P, Zhang L, Nakajima M, Kaneda Y, Cooke J P, Dzau V J: Gene therapy inhibiting neointimal vascular lesion: In vivo transfer of endothelial cell nitric oxide synthase gene. Proc Natl Acad Sci USA 1995;92:1137–41

Wang B-Y, Singer A, Tsao P, Drexler H, Kosek J, Cooke J P: Dietary arginine prevents atherogenesis in the coronary artery of the hypercholesterolemic rabbit. J Am Coll Cardiol 1994;23:452–58

Winter G, Griffiths A D, Hawkins R E, Hoogenboom H R (1994) Making antibodies by phage display technology. Ann. Rev. Immunol. 12: 433–456

Wolfe A, Theilmeier G, Zalpour C, Ma A, Anderson B, Wang B-Y, Candipan R C, Tsao P S, Cooke J P: Platelet hyperaggregability in hypercholesterolemic humans: Reversal by dietary L-arginine. Annals of Int Med (under review) 1995

Youn H J, Terpetschnig E, Szmacinski H, Lakowicz J R Fluorescence energy transfer immunoassay based on a long-lifetime luminescent metal-ligand complex. Anal Biochem 1995 November 20;232(1):24–30

Yu X, Li Y, Xiong Y: Increase of an endogenous inhibitor of nitric oxide synthesis in serum of high cholesterol fed rabbits. Life Sci. 1994;54:753–758

Zeiher A H, Drexler H, WollschlEger H, Saurbier B, Just H: Coronary vasomotion in response to sympathetic stimulation in humans: Importance of the functional integrity of the endothelium. J Am Coll Cardiol 1989;14:1181–1190

What is claimed is:

1. A method for measuring the amount of asymmetric dimethylarginine (ADMA) in a physiological sample, said method comprising:

removing interfering components from said sample;

contacting said interfering component-free sample with dimethylarginine dimethylamino-hydrolase (DDDH)

in an amount sufficient to hydrolyze said ADMA to citrulline; and spectrophotometrically determining said citrulline, whereby the amount of citrulline is related to the amount of ADMA in the sample.

2. A method according to claim 1, wherein said physiological sample is plasma.

3. A method according to claim 2, wherein said removing step comprises:

treating with arginase;

precipitating proteins present in said plasma; and passing said protein-freed plasma through a mixed phase cation exchange and hydrophobic interaction cartridge.

4. A method according to claim 3, wherein ADMA is eluted from said mixed phase cation exchange and hydrophobic interaction cartridge with triethylamine.

5. A method according to claim 3, wherein said precipitating is with an acidic solution.

6. A method according to claim 1, wherein said DDAH is recombinantly prepared.

7. A kit comprising DDAH, and reagents for spectrophotometrically determining citrulline.

8. The kit according to claim 7, further comprising a mixed phase cation exchange and hydrophobic interaction cartridge.

* * * * *